United States Patent
Kruse et al.

(10) Patent No.: US 9,238,100 B2
(45) Date of Patent: Jan. 19, 2016

(54) DEVICE AND METHOD FOR TRAINING USERS OF AMBULATORY MEDICAL DEVICES

(71) Applicant: Tandem Diabetes Care, Inc., San Diego, CA (US)

(72) Inventors: Geoff Kruse, San Diego, CA (US); Kim Blickenstaff, San Diego, CA (US); Mike Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 124 days.

(21) Appl. No.: 13/828,958

(22) Filed: Mar. 14, 2013

(65) Prior Publication Data

US 2013/0331778 A1   Dec. 12, 2013

Related U.S. Application Data

(60) Provisional application No. 61/656,984, filed on Jun. 7, 2012.

(51) Int. Cl.
*A61M 5/14* (2006.01)
*A61M 5/172* (2006.01)
*A61M 5/142* (2006.01)

(52) U.S. Cl.
CPC ......... *A61M 5/1413* (2013.01); *A61M 5/14244* (2013.01); *A61M 5/1723* (2013.01); *A61M 2205/502* (2013.01); *A61M 2205/52* (2013.01)

(58) Field of Classification Search
CPC ... A61M 2230/201; G06F 3/14; G06F 3/1454
USPC .............................................. 604/65–67, 151
See application file for complete search history.

(56) References Cited

U.S. PATENT DOCUMENTS

| | | | |
|---|---|---|---|
| 8,032,226 B2 | 10/2011 | Miller et al. | |
| 2002/0019606 A1* | 2/2002 | Lebel et al. | 604/66 |
| 2005/0171512 A1 | 8/2005 | Flaherty | |
| 2006/0184154 A1 | 8/2006 | Moberg et al. | |
| 2007/0118405 A1 | 5/2007 | Campbell et al. | |
| 2009/0177147 A1 | 7/2009 | Blomquist et al. | |
| 2009/0177154 A1 | 7/2009 | Blomquist | |
| 2011/0033833 A1 | 2/2011 | Blomquist et al. | |
| 2011/0133946 A1 | 6/2011 | Kopp et al. | |
| 2012/0029433 A1 | 2/2012 | Michaud et al. | |

OTHER PUBLICATIONS

Search Report and Written Opinion dated Nov. 6, 2013 for PCT Application No. PCT/US2013/044319 filed Jun. 5, 2013, 12 pages.
International Preliminary Report on Patentability dated Dec. 9, 2014 for PCT Application No. PCT/US2013/044319 filed Jun. 5, 2013, 6 pages.

* cited by examiner

*Primary Examiner* — Nicholas Lucchesi
*Assistant Examiner* — Melissa A Snyder
(74) *Attorney, Agent, or Firm* — Patterson Thuente Pedersen, P.A.

(57) ABSTRACT

Apparatuses and methods for training users of ambulatory medical devices. The methods relate to improving user interactions with the touchscreens of devices. In one embodiment there is an operating mode that records all user interactions along with various device parameters and allows the clinician to review the patient's performance for the initial use period. Automated analysis software may be employed to analyze the data generated by the device. The results of the analysis may be used by the clinician to improve the patient and device interaction.

18 Claims, 6 Drawing Sheets

DEVICE AND METHOD FOR TRAINING USERS OF AMBULATORY MEDICAL DEVICES

RELATED APPLICATION

The present application claims the benefit of U.S. Provisional Application No. 61/656,984 filed Jun. 7, 2012, which is incorporated herein in its entirety by reference.

BACKGROUND

Portable ambulatory medical devices have proved useful for treating patients with medical conditions that require continuous monitoring and/or treatment. One example of such a portable ambulatory medical device is a device that involves the delivery of fluids. There are many applications in academic, industrial, and medical fields, as well as others, that involve devices capable of accurately and controllably delivering fluids, including liquids and gases, that have a beneficial effect when administered in known and controlled quantities. This is particularly true in the medical field, where treatments for many patients include the administration of a known amount of a substance at predetermined intervals. For example, the treatment of diabetes involves just such a regimented dosage of medicaments such as insulin. In addition, diabetes is one of a few medical indications wherein the patients routinely administer the medicament to themselves by a subcutaneous modality, such as a hypodermic syringe injection or by an ambulatory infusion pump. As such, providing a patient with the means to safely, reliably, and comfortably administer required doses of medication such as, e.g., insulin, may be particularly important in order to facilitate patient compliance and accurate treatment of the condition.

Ambulatory infusion pumps have been developed for the administration of medicaments such as insulin for those diagnosed with both type I and type II diabetes. These pumps offer an alternative to multiple daily injections of insulin by an insulin syringe or an insulin pen. They also allow for continuous insulin therapy. In addition, some ambulatory infusion devices can include data collection and storage mechanisms, which allow a diabetic patient/user and/or a caregiver (e.g., doctor, health care worker, family member, and so forth) to easily monitor and adjust insulin intake. The infusion device may be powered by a rechargeable battery that requires periodic recharging.

Ambulatory medical devices may include a keypad, buttons, and/or touchscreen with a display on which symbols may be displayed and from which inputs may be received for operation of the device. A series of display screens or windows may be displayed on the touchscreen, showing alphanumeric text and symbols and providing menu screens through which the user can control operation of the device and receive information regarding the device and its operation, history, settings, interaction with the user, and the like. User interaction, such as by touching the alphanumeric text and symbols, provides user input and facilitates navigation through the menu screens and selection of the device functions.

With the advancement of medical devices and the increasing complexity of the user interfaces, some users may experience difficulty interacting with the user interface of the device, such as, for example, when entering inputs to operate the device. It is desirable to reduce the number of user errors and minimize the consequences of such errors. One difficulty users can experience, particularly when interacting with touch screen user interfaces, is the accidental touch of adjacent buttons/icons. A unique complication that may be present with respect to diabetic users for ambulatory insulin pumps is that these users may build up calluses on the tips of their fingers as a result of repeated blood glucose testing. Such calluses may be especially problematic for the operation of capacitive-based touch screen pump configurations. For example, calluses may prevent or hinder the transfer of energy that the capacitive screens use to receive input, thus preventing or hindering proper use of the touch screen to control the pump by the user.

To compensate for such difficulties in operation and provide improved user interface configurations, it is common in user interface research to observe and record the user inputs for performing a given task. One of the primary methods employed to aid this analysis is the use of external video cameras to record the user input over a period of time. The resulting data analysis can be tedious, as the analysis requires, e.g., comparison of the recorded touch sequence to an ideal task sequence. Any deviation from the expected task pathway may be noted as user error. Analysis of such deviations is then used as a design input to improve the accuracy of the human interface input.

Ambulatory infusion pumps with user interlaces implemented and incorporated therein enable the patient to administer the medicament, such as insulin, to themselves. For proper operation by a user of the device, it is important that the user be adequately trained with regard to the device operation. Some users, including patients and/or caregivers, may not be adept at operating such pumps, even if they are designed for simplicity and ease of use, and may require training to ensure proper operation of the device and efficacious treatment of their medical condition. Users, including patients and/or caregivers, may experience further complications with particular devices, such as insulin delivery systems, because each individual user responds uniquely to a given insulin dosage and rate of dosage. Such devices often require training so the patient does not over-medicate or under-medicate in myriad unique "real life" scenarios. Thus, with the rapid advancement and proliferation of such portable ambulatory medical devices, there is an associated need for increased training and clinician support.

Current trends in the delivery of health care are toward reduced patient medical support and, for operation of devices such as ambulatory medicament pumps, reduced training of users. This reduction is due in part to the overloading of health care resources such as hospitals, medical professionals, and caregivers, increasing financial limitations for access to medical care, rising healthcare costs, and a shortage of well-trained clinicians and caregivers.

In view of the discussion above, there is a need for systems and methods to more effectively train users, including patients and caregivers, for efficacious operation of ambulatory medical devices to accommodate each individual patient with unique circumstances and responses to therapy and to do so with reduced support from clinicians and others, including, e.g., representatives from the manufacturer of such ambulatory medical devices (such as field clinical support personnel, customer service representatives, certified diabetes educators (CDEs), sales representatives, etc.).

In view of the discussion above, there is also a need for systems and methods to improve the accuracy, efficiency and capability of the user interface system beyond the recording and play back analysis methods currently used in touch interface development.

SUMMARY

Disclosed herein are devices, such as ambulatory portable medical devices (e.g., ambulatory pumps for the administration of insulin and other medicaments for the treatment of diabetes), and methods of improving the interaction of such devices with users. The portable device may include control features such as buttons or switches to control pumping and other factors, and the portable device may include a touch screen on which are displayed alphanumeric text, symbols, menu screens, data, alerts and other information. While in operation, the device provides features such that it receives user input and detects device parameter values at the time of the user input. The device writes the received user input and the device parameter values into memory of the device. The features may be provided in an operating mode of the device, or the features may be provided as a function or application within an operating mode of the device.

For example, the device may have one or more modes of operation including a training simulation mode, a normal operating mode, and an initial operating mode. The device may include a processor and system bus, and may also connect compatible external sensors to the system bus for gathering and storing device parameter data. In one embodiment, a normal operating mode of the device detects user interactions and records the interactions along with various device parameters at the time of the interaction, and allows a clinician to review the user's performance for the initial use period. Automated analysis software may operate to analyze the data generated by the user during the normal operating mode. The results of the analysis may be used by the clinician to improve the user and device interaction. This can be done by changing settings in the device, and/or providing additional training to the user.

Other features and advantages of the present invention should be apparent from the following description of preferred embodiments that illustrate, by way of example, the principles of the invention.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Disclosed herein are embodiments directed to a portable medical device having an interactive display screen, such as a touchscreen, for control by the user, and having a connecting tube with an infusion port for administering medication to a patient.

Figure 1:
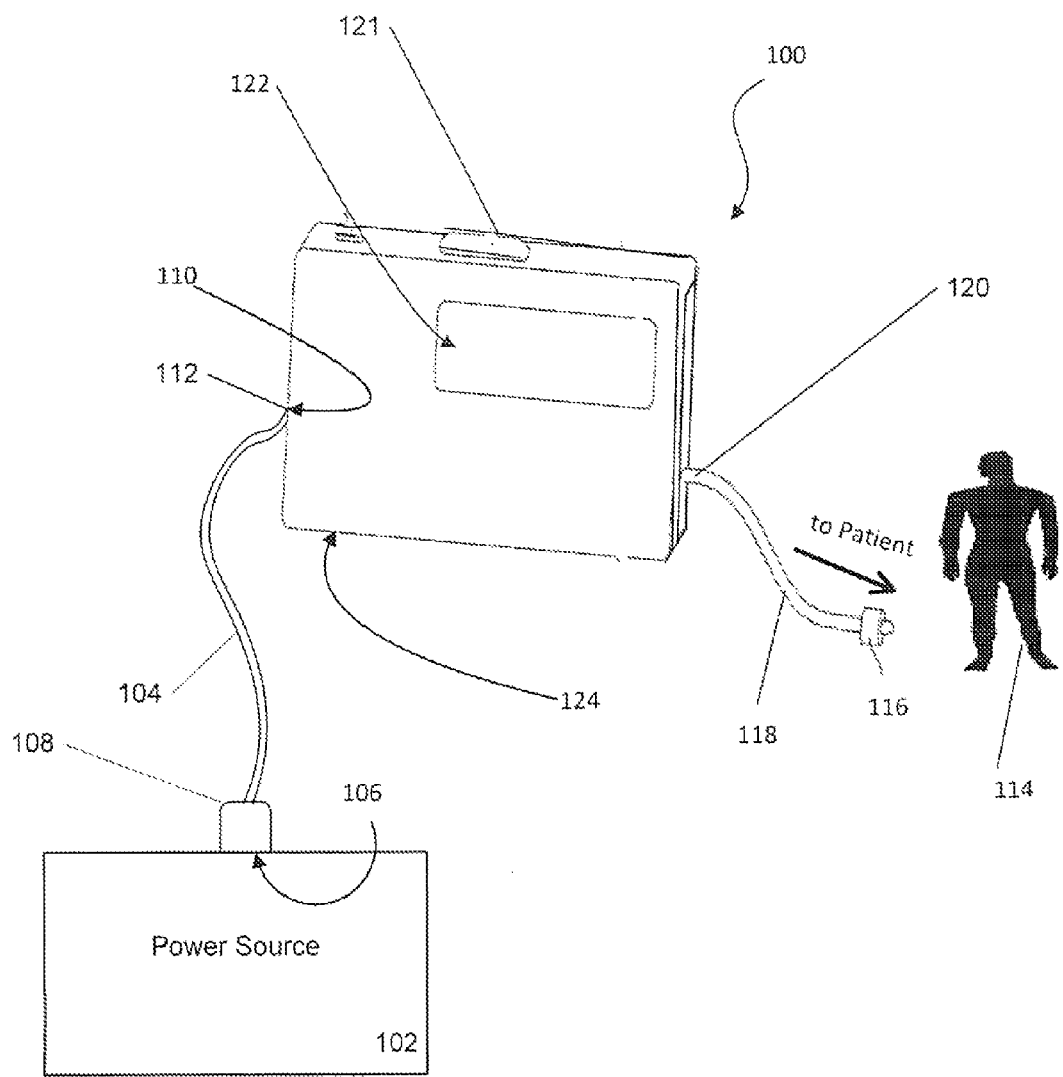
FIG. 1 depicts a portable device according to an embodiment of the present invention that is coupled to a patient for infusing medication thereto.

FIG. 1 depicts an electrically-powered portable device 100 that is coupled to a host power source 102, such as a desktop or laptop computer, through a cable 104. The cable may comprise, for example, a coupling through which both data and electrical energy are received at the portable device 100. Examples of such combined power and data cables include a Universal Serial Bus (USB) connection, an IEEE 1499 connection, a "THUNDERBOLT" connection (i.e., from Apple, Inc., of Cupertino, Calif., USA), PCI Express, eSATA and Ethernet. The host power source 102 is a source of electrical energy and the host computing device can be any type of computing device that includes a port 106 that receives a connector 108 of the cable 104. The port of the host computing device may comprise, for example, a USB port, or IEEE 1499 port, or port for THUNDERBOLT, PCI Express, eSATA and Ethernet. A compatible connector port 110 of the portable device 100 is coupled to the cable 104 at an opposite end 112 of the cable. In a USB implementation, for example, the cable 104 is a USB 5 cable and associated connections and ports may support one or more of USB version 1.1, 2.0, or 3.0 data transfer speeds.

The portable device 100 may be coupled to a patient 114 via an infusion port 116 and a connecting tube or cannula 118. The connecting tube is coupled to the portable device 100 at a fluid dispensing port 120. The portable device may include control features, such as buttons or switches 121 to receive user input and control pumping and other functions, and may include a display screen 122 on which messages and alerts are displayed. The display 122 may comprise, for example, a touchscreen on which user inputs may be received. A housing 124 of the portable device encloses internal components, such as fluid reservoirs, electrical components, battery, and the like. The portable device 100 illustrated in FIG. 1 comprises a portable medical device of the type worn by a patient 114 such that fluid such as insulin is delivered via the connecting tube 118 and the fluid dispensing port 120. Exemplary ambulatory medical devices and features include those, e.g., disclosed in U.S. patent application Ser. Nos. 13/557,163, 12/714,299, 12/538,018, U.S. Provisional Patent Application No. 61/655,883, U.S. Provisional Patent Application No. 61/656,967 and U.S. Pat. No. 8,287,495. Each of the aforementioned documents is hereby incorporated herein by reference in its entirety.

The portable device 100 can be coupled to a host power source such as a desktop or laptop computer, through a cable connected to the connector port 110. The cable may comprise, for example, a coupling through which both data and electrical energy are received at the portable device 100. Examples of such combined power and data cables include a Universal Serial Bus (USB) connection, an IEEE 1499 (FireWire) connection, a "THUNDERBOLT" connection (from Apple, Inc. of Cupertino, Calif., USA), PCI Express, eSATA and Ethernet.

The device 100 may also include a capability to operatively couple to one or more other devices via a wired or wireless (e.g., infrared, electronic, optical, etc.) link, locally or via a network, such as, e.g., a portable or non-portable medical device, a control unit, external monitor or display, a personal, laptop, tablet or mainframe computer, or mobile communication device such as a smartphone or personal digital assistant (PDA). Such other devices may control or be controlled by device 100 and/or may otherwise communicate for the transfer of data including device parameters between or among device 100 and other device(s) for analysis of data (e.g., user data for physician review, device diagnostic data for troubleshooting or repair), programming, or other uses.

The portable device 100 may include control features such as buttons, panels, screens, and/or switches to control pumping and other functions, or any combination of such control features. For example, the portable device 100 illustrated in FIG. 1 shows a touchscreen 122 on which can be displayed alphanumeric text, symbols, menu screens, data, alerts and other information for receiving control input. The portable device may include a processor with memory, wherein the processor executes program instructions to provide an operating system that supports programs that execute and provide the specified features. The touchscreen 122 may be interactive, wherein user input may be received such as by pressing the outer surface of the touchscreen. The touchscreen 122 may be configured to display menu screens or pages that allow the user to input data fields to, e.g., select device parameters, so as to allow the program to produce a suggested delivery amount, rate, profile, and/or the like in an intuitive, manipulatable, and/or graphic representation. The user can therefore interact with the screen to shape the characteristic/form of the delivery amount, rate, and/or graphic delivery profile, e.g., by manipulating the delivery estimate or pattern displayed on the screen to effectuate the actual delivery.

Figure 6:
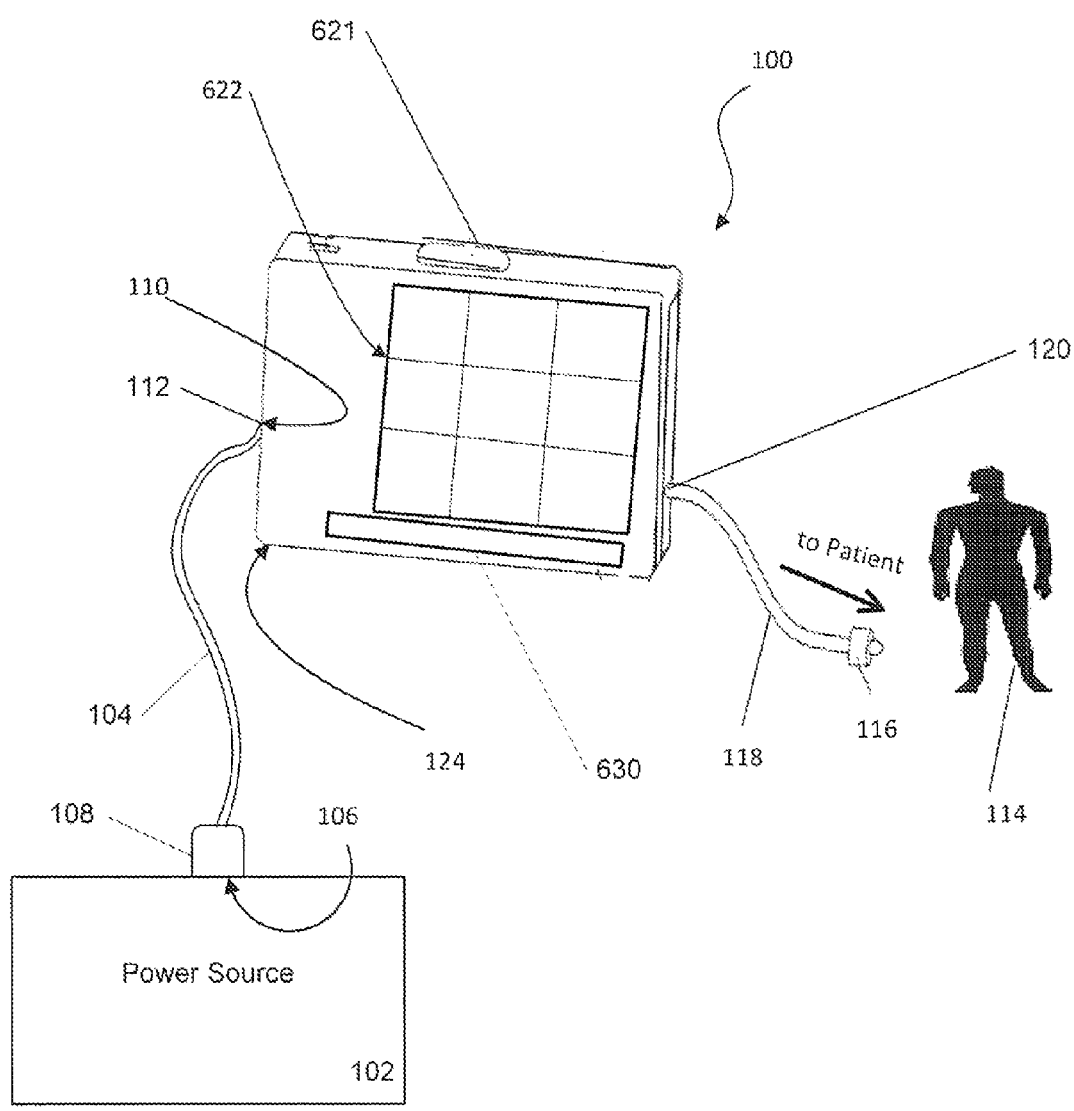
FIG. 6 depicts a keyboard-equipped portable device that is coupled to a patient for infusing medication thereto.

FIG. 6 depicts an embodiment of a portable device 600 that is coupled to a host power source 102, such as a desktop or laptop computer, through a cable 104, and is similar in construction to the embodiment illustrated in FIG. 1, except that the FIG. 6 device 600 has control features that are physical buttons, including a power switch 621 and a keypad 622 that the user presses to control the device, including actions such as pumping and the like. The device 600 includes a display 630 on which indications are displayed. Structures in FIG. 6 with like reference numerals to those in FIG. 1 relate to like structures.

Device parameters provided by the portable infusion device may be presented on the display screen 122 as any number of objects, including one or more numeric and/or alphanumeric values, a range, a value or range that is presented in the form of a drop-down menu, a toggle that can be adjusted by the user, a graphical representation (e.g., icon) or an animated graphic. For instance, in certain embodiments, the value is a range of values that are presented on a screen of the display as a toggle, wherein the toggle may be adjusted upwards or downwards by the user swiping a finger over the screen to select the appropriate value range, e.g. appropriate range of amounts of medicament such as insulin to be delivered and/or the appropriate rate, time, or interval of medicament delivery. In certain instances, the values presented in the range may be adjusted by the processor (illustrated in FIG. 2). Other device parameters will be readily apparent to those skilled in the art.

If the device includes a touchscreen 122 as in FIG. 1, the type of touchscreen may be selected as desired to be useful for a particular application, such as touchscreens comprising LCD displays, LED displays, plasma displays, organic LED (OLED) displays, and the like. The touchscreen 122 may be implemented with a capacitance screen, a resistive screen, or other such display/input technology. The portable device 100 may additionally include a keyboard or other input device known in the art for data entry, which may be separate from the display.

Figure 2:
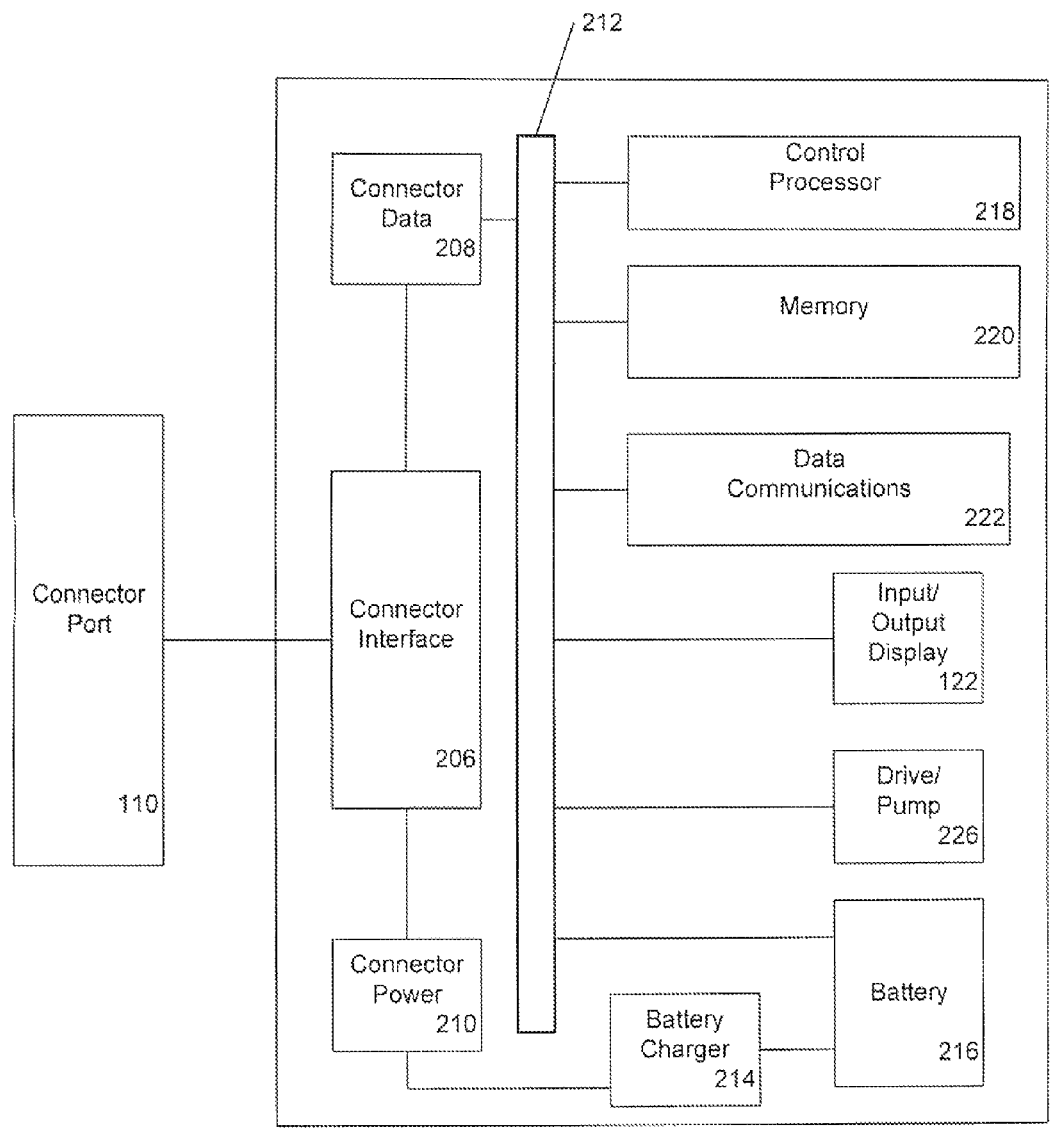
FIG. 2 is a block diagram of circuitry and components for the portable medical device of FIG. 1.

FIG. 2 depicts a block diagram of some of the components within the portable device 100 of FIG. 1. The portable device 100 includes a power management system 202 that is connected to the connector port 110 that receives a combined data/power cable, such as the USB cable 104 illustrated in FIG. 1. That is, the cable 104 has the capability of simultaneously providing electrical energy for charging and data transmission for communications. A connector interface 206 supports data exchange and receives electrical power through the connector port 110, and controls a connector data element 208 and a connector power element 210. The device may be powered by battery power in place of or in addition to the connector interface. The connector interface 206 passes data communications from the connector port 110 through the connector data element 208 to a system bus 212. The connector interface 206 passes electrical power from the connector port 110 through the connector power element 210 to a battery charger 214, which in turn is coupled to a battery 216 and which recharges the battery. In one embodiment, the connector data element 208 is implemented in the FIG. 2 device with a USB Isolation Chip ADUM4160 product from Analog Devices, Inc. of Norwood, Mass., USA, and the connector power element 210 is implemented in the FIG. 2 device with a USB Power Isolation Chip LT3573 product from Linear Technology Corporation of Milpitas, Calif., USA. Those skilled in the art will be aware of alternative suitable devices.

A control processor 218 is connected to the system bus 212 and receives the data communications from the connector data element 208 for processing. The control processor controls operation of the various elements of the portable device 100 that are connected to the system bus. The control processor operates according to mode instructions that may be stored in device memory 220.

During operation of the device according to typical usage, such as when the device provides the actions for which it is designed, the device provides features such that it receives user input and detects device parameter values at the time of the user input and writes the received user input and the device parameter values into memory of the device. In the case of a portable infusion pump, for example, the operational actions include pumping medicaments such as insulin to a patient. The parameter detecting and memory writing features of the device may be provided in an operating mode of the device, or they may be provided as a function or application within an operating mode of the device. The phrases "mode" and "function" may be used interchangeably, as required by context, as will be known to those skilled in the art.

The devices of FIG. 1 and FIG. 6 may each have one or more modes of operation. That is, each device may be capable of operating in one mode exclusively or in one or more modes simultaneously. The parameter detecting and memory writing features of the device, however, are provided in conjunction with a mode or function of the device in which the device provides the actions for which it is designed. For example, the parameter detecting and memory writing features may be provided in an operating mode of the device, such as a normal operating mode, or may be provided in a function, such as a recording function, of a single or of multiple modes.

For example, the device may have a normal operating mode where the device is attached to the patient and the device is capable of receiving and responding to user interaction, and delivering medicament as required. The device may also have a training mode in which the device may or may not be coupled to the patient and the clinician can simulate scenarios on the device while monitoring the patient's interactions with the device. The parameter detecting and memory writing features of the device as described herein would not ordinarily be available in the training mode, absent a function that permits the device to operate so as to provide the actions (e.g., pumping) for which it is designed.

The parameter detecting and memory writing features may be provided autonomously by the device, without input from the user, or providing the parameter detecting and memory writing features may require specific input from the user. In the case of specific input from the user, the parameter detecting and memory writing features may be provided as a function of the normal operating mode, initiated through a special configuration by an authorized clinician or other suitable person and comprising a temporary modification to the normal operating mode. Alternatively, the parameter detecting and memory writing features can be initiated from the time of initial power-on of the device, and continuing on for a predetermined subsequent time, at which time the parameter detecting and memory writing features are terminated. Alternatively, the device may continually monitor patient performance, without termination of the parameter detecting and memory writing features, providing a mode of operation that facilitates review of user performance at the time of a call to customer service or other request for assistance. The device may also have a playback function, wherein a user, caregiver, clinician, or the like can review data stored in the device memory.

Program instructions may be stored in processor memory incorporated in the control processor 218. The control processor also stores data including device parameters, from its operations in the device memory 220. The control processor 218 controls a data communications element 222 that may comprise a receiver/transmitter for wireless RF communications, such as "WiFi" communications or "Bluetooth" communications between the portable device 100 and compatible external systems and networks. The communications may take place over proprietary networks or links, or may take place using secure links over public networks. The device 100 includes an output/display element 122 such as a touchscreen display, operating buttons or switches. The device 100 of FIG. 1 comprises an infusion pump device, and therefore also includes a drive/pump element 226 such as a pumping mechanism for delivery of fluid such as insulin to the connecting tube 118, as described above in connection with FIG. 1. To meet industry standards and governmental regulations, the connector data element 208 and the connector power element 210 are both electrically isolated from the other device components, so as to provide a device that can be safely connected to the power source and the patient at the same time.

The device may also connect compatible external sensors to the system bus 212 for gathering and storing device parameter data. The device parameter data can be used as an input to the processor to make automated decisions, it can be reported to the user through the touchscreen 122 to aid the user in making self-medicating decisions, or it can be recorded into memory 220 for later analysis. The data may also be sent to a third party or another device for monitoring the patient's status. Other uses of such data are well known and are readily apparent to those skilled in the art. The external sensors can be any type of sensors useful for the operation of the device, such as optical, electrical, mechanical, electro-mechanical and chemical. The external sensors may be, e.g., traditional physical sensors that monitor body temperature, blood pressure, and the like, or they can be sensors that utilize chemical or biological reactions. Chemical and biological sensors differ from physical sensors, which are limited to the measurement of basic physical parameters. An exemplary and well-known chemical or biosensor is an enzyme electrode for the detection of glucose. These sensors are typically comprised of a bioactive surface consisting of immobilized glucose oxidase sandwiched between a polycarbonate and cellulose acetate membrane. The transducer is a platinum electrode and the output is typically a low current on the order of microamperes. Myriad chemical and biological sensors are available and are well known in the art such as Ph sensors for in vivo blood gasses, fiber-optic glucose sensors, biosensors based on transition metal hexcyanoferrates and chemically prepared grapheme-based nanomaterials.

The memory 220 of the device 100 may be any type of memory capable of storing data and retrieving that data for transfer to one or more other components of the device, such as the control processor 218. The memory may comprise one or more of a Flash memory, SRAM, ROM, DRAM, RAM, EPROM and dynamic storage. For the illustrated portable fluid delivery device 100 of FIG. 1, the device memory 220 may be coupled to the control processor 218 and may be configured to receive and store one or more device parameters comprising, e.g., user input data from the touchscreen, user input from buttons or switches, time, date, external sensor readings, device operating status, device messages to the user, user templates or predetermined fluid delivery patterns. The device parameters may be stored as a discrete data set at a particular point in time, a multitude of sequential discrete data sets separated by a period of time, or what is effectively termed "real-time" or continuous recording of the device parameters as fast as the system will allow. Other methods of recording device parameters such as initiating a recording based upon a trigger event are readily apparent and well known to those of skill in the art.

The memory can also be configured to store one or more personalized (e.g., user defined) delivery profiles, such as a profile based on a user's selection and/or grouping of various input parameters; past generated delivery profiles; recommended delivery profiles and one or more traditional delivery profiles, e.g., square wave, dual square wave, basal and bolus rate profiles. The memory can also store other device parameters such as user information, history of use, glucose measurements including blood glucose data and continuous glucose monitoring data, compliance and a calendar of events. An infusion workflow, or protocol, may be at least part of a program that displays a sequence of menu pages to assist a user to at least program or control the portable infusion device and/or at least one operation comprising input, change, confirm, or view various information within the device. Any part of a workflow or protocol may include any number of queries for prompting the user to enter, modify, or confirm information, which are typically presented to the user on the touchscreen display. In some embodiments, the memory 220 of the portable medical device 100 may have a data capacity of up to about 10 GB, more specifically, up to about 3 GB, even more specifically, about 1 MB to about 200 MB. In some embodiments, the memory of the infusion device 200 may be up to about 3 GB, more specifically, up to about 500 MB or more, and even more specifically, about 200 kB to about 200 MB. Larger memory sizes will permit more extensive use and operating modes, such as continual use in recording device parameters and/or user interactions, rather than initial use.

Figure 3:
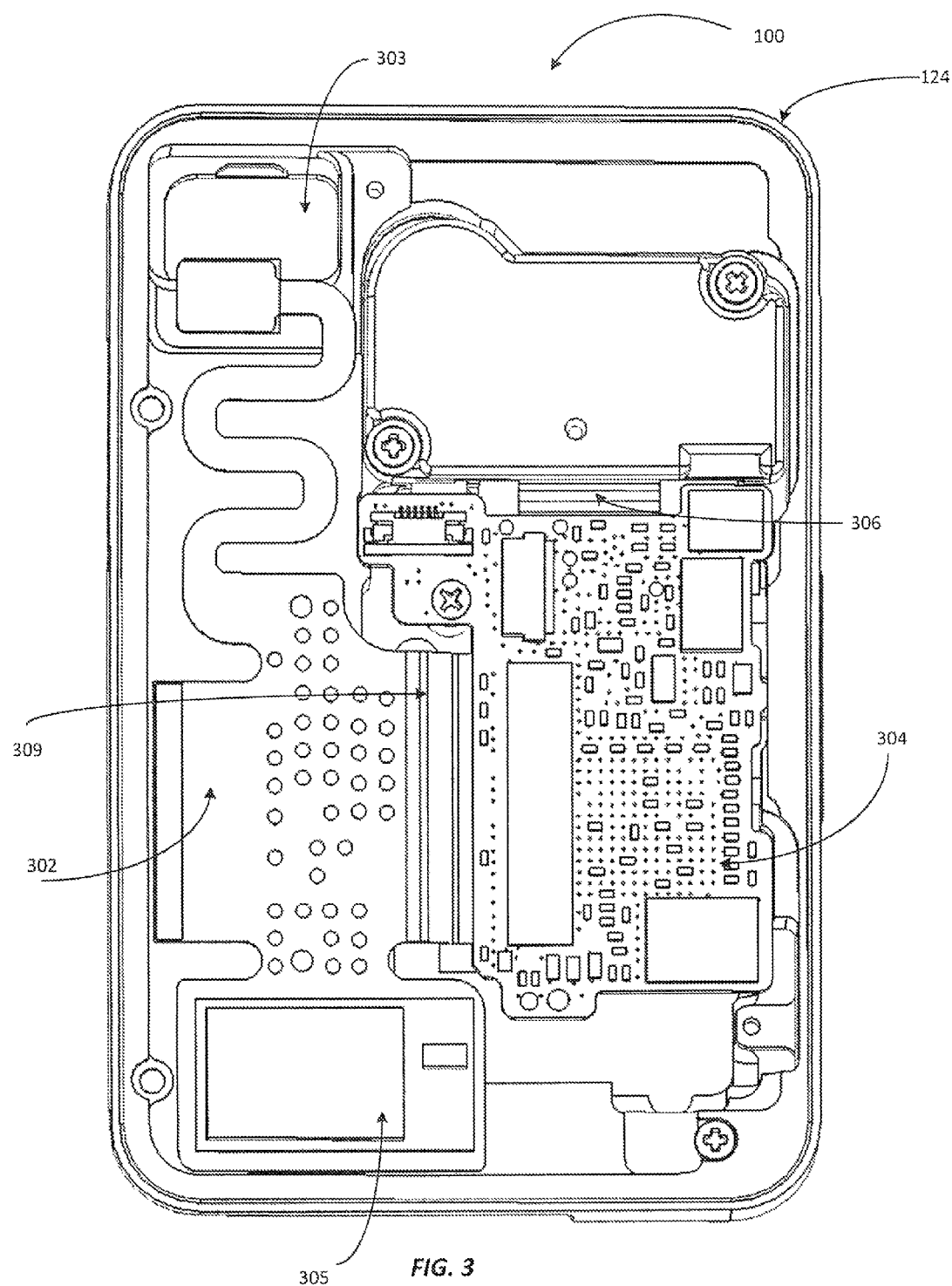
FIG. 3 is a schematic that depicts the circuitry and components of a portable medical device with the front side housing removed as in FIG. 1.

FIG. 3 provides a schematic representation of the device depicted in FIG. 1 with the front face of the housing 124 removed and the internal components exposed. As shown, the portable medical device 100 includes a printed circuit board (PCB) assembly including a flex serpentine board 302, a main board 304, a connector for the Hex board and main board to direct current (DC) 306, a pressure board 303, and a connector for the flex board to the pressure board 309. Additionally, the device includes a Bluetooth PCB assembly 305 for short wave, such as radio frequency (RF) communication. Such communication can be useful if a user of the device wishes to transfer data to, for example, a Bluetooth-enabled mobile telephone, such as a Smart Phone.

Figure 4:
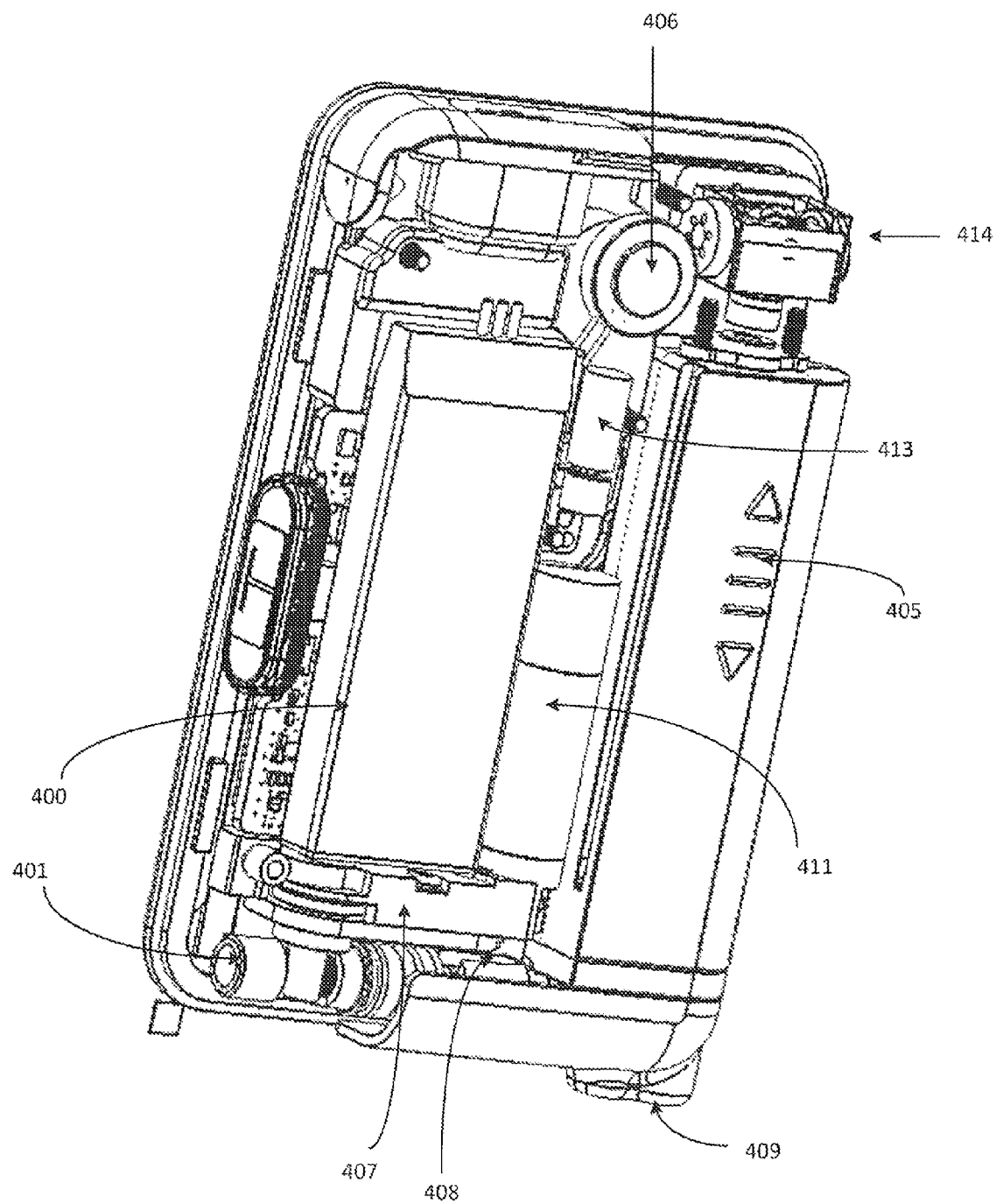
FIG. 4 is a schematic that depicts a perspective view of the device of FIG. 1, having the back face of the housing removed.

FIG. 4 is a schematic view of the back of the portable medical device in FIG. 1 with the rear face removed. As shown in FIG. 4, the various elements controlled by the PCB on the front schematic view in FIG. 3 are provided. The device can include a speaker 406 and vibrate mechanism 413 for providing alerts and other sounds indicating a function has been performed on the device. Additionally, the device can include a micro-valve assembly 414, including, for example, a venting system and a thermal leak platform for the insulin cartridge. The insulin cartridge can be covered by a cartridge door 405 and the housing of the portable medical device can include a cartridge shroud 409 in which the connecting tube 118 delivering the insulin to the patient may be inserted. Additionally, the device can include a power charging system, which receives the controlled current from the power isolation chip. The power charging system may be used to charge a power storage cell such as a rechargeable battery 400 of the portable medical device. Some embodiments may use a rechargeable battery such as a NiCad battery, LiPo battery or NiMH battery.

The device 100 comprises an infusion pump device, and therefore also includes a drive/pump element such as a pumping mechanism for delivery of fluid such as insulin to the connecting tube 118, as described above in connection with FIG. 1. In FIG. 4 several of the pump device components are depicted such as a pump motor 411, rack bushing 401, rack pushrod 408 and gear box 407. The device is not limited to these components and fewer or additional components may be employed depending upon the particular operating requirements of a device.

Figure 5:
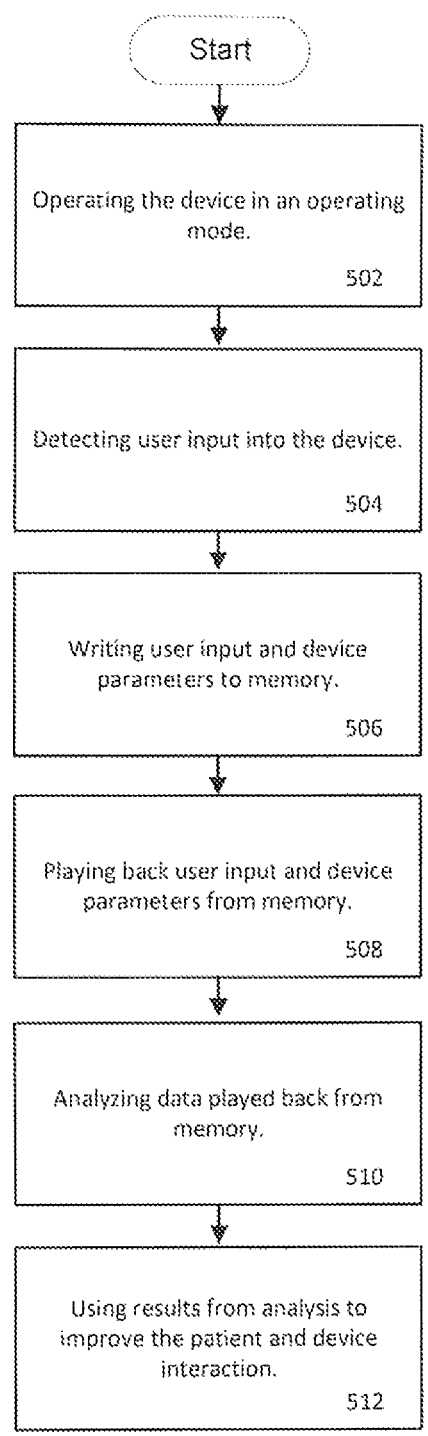
FIG. 5 is a flowchart showing an embodiment of the invention wherein there is an operating mode that provides a method to record all user interactions and allow the clinician to review the patient's performance for the initial use period.

FIG. 5 is a flowchart that illustrates a method of use of a device such as the devices 100, 600 described herein. The operations are performed such that all user interactions are detected and recorded. Such parameter detecting and memory writing features, as described previously, permit a user, caregiver, clinician, trainer, and the like to review the recorded user performance. After the portable medical device as described herein is attached to a patient, at the operation 502, the device is placed in operation. Next, at step 504, the user interacts with the device either through a button, a touchscreen, or other input mechanism. The user interaction may comprise, for example, selecting a function, providing an input or navigating through the user interface. In step 506 the device detects the user interaction and stores the user interaction, including any button press, touchscreen interaction, etc., in the device memory. Optionally, additional device parameters can be stored in memory, such as a timestamp for time of day, external sensor readings indicating body temperature, blood glucose level, blood pressure, glucose level data from a continuous glucose monitor and others, as described herein above. The recording can simply be a "snapshot" of the user input and selected device parameters at that particular time, or the device may take numerous sequential "snapshots" separated by a period of time. For a sequence of snapshots, the timestamp recorded with each interaction will indicate the passage of time between consecutive user interactions. Optionally the device may be programed to continuously record data for a predetermined period of time after a first user interaction. Further, the device may be programmed with a continuous F.I.F.O. (first in first out) buffer that maintains a predetermined amount of data in memory and, upon user interaction, stores data starting at a predetermined period of time (e.g. initiated by the user) and continuing to 5 a period of time after the user interaction. Numerous other methods of capturing data are readily known by those of skill in the art.

In step 508 the stored data can be played back in a playback mode on the device itself, or the stored data can be transferred from device memory to a separate device, such as a computer, for playback. In step 510 the user interaction with the device can be analyzed for potential or actual errors. The analysis can be performed on a screen-by-screen basis or through analysis software that processes all the stored user interactions and provides an automatic summary of the patient's therapy. The analysis software may reside on an external device or may be installed at the device itself. The analysis operations of the software may be applied to stored or historical data. The analysis may be applied in real-time as the patient is operating the device, to provide an indication of how well the patient is operating the device. The automated analysis can identify "close calls" where the patient changes the therapy at the last moment, "difficulties" where the patient deviates significantly from an optimum path or "errors" where the patient initiates a therapy or setting that does not match the instructions of a trainer or caregiver. The analysis software may provide an indication of trending, that is, an evaluation of how well the patient is interacting with the user interface. It would be expected that patient performance in terms of errors would improve most greatly during an initial period and then would stabilize over time. If the system detects that the patient is regressing, such as an increase in observed errors, then the system may provide a notification of patient difficulty or regression. Other pertinent issues can readily be identified by the analysis software and are known to those of skill in the art. In step 512, the results of the analysis are used by the trainer, patient, clinician, caregiver or the like, to improve the user-device interaction. For example, improvement may be achieved by changing settings in the device, and/or providing additional training to the user.

The benefits of the parameter detecting and memory writing features during operation should be readily apparent as compared to a conventional training mode of operation. In a training mode, the device may not be coupled to the patient, or if coupled, may not be operational, and thus the user interaction scenarios are simulated and are likely not representative of that particular user's responses in a medicament delivery context. Complications can arise with medicament delivery devices such as insulin pumps because each individual user or patient responds uniquely to a given insulin dosage and rate of dosage. Additionally, each patient has a unique lifestyle, which may not be considered in the training mode. For instance, some patients have the ability to self-manage their dependency on insulin such as sensing when blood sugar is low and eating particular foods with carbohydrate levels and types adequate to safely increase their blood sugar levels. In such a scenario, the insulin delivery device may initiate therapy when it is not required, hence risking over-medication of the patient. Conversely, other patients may require significant dependence on insulin because of poor eating habits or the lack of the ability to self-manage their disease. In these scenarios the insulin delivery device may deliver too little insulin too late, thus risking under-medication of the patient.

Therefore the parameter detecting and memory writing features of operation described herein provide an individualized "fine tuning" or customization of the relationship between a patient and their device. This kind of fine tuning typically requires extensive support from trainers, clinicians, and/or other caregivers to interact with the patient on a frequent basis. However, with the ability of the device to capture user interactions along with the device parameters, the trainer, clinician and/or other caregiver can expediently identify and analyze only the relevant areas for improvement. Further, with automated analysis software, the trainer, clinician, and/or other caregiver can even more expediently identify the areas of concern and efficiently fine tune those particular areas of the user interaction. Thus, this method can effectively train patients, each with their unique circumstances and individualized response to therapy, how to efficaciously operate ambulatory medical devices while requiring reduced support from clinicians.

Although the aforementioned description specifically describes a portable medical device for administering insulin to a patient, it should be understood that such a device is only one embodiment of the invention. The device can also include any portable device having a display and a processor. For example, the device can include a mobile computing device, such as a Smartphone. In one embodiment, such a mobile computing device can function as a remote control for a portable medical device as described herein. Alternatively, a dedicated remote control specifically designed for use with a portable medical device can be used to control the device.

The methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures. Each operation of a process is performed or executed by the processor of the device.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

The invention claimed is:

1. An ambulatory infusion pump, comprising:
a housing;
a delivery mechanism at least partially contained within the housing and adapted to facilitate delivery of fluid to a user;
a user interface adapted to receive user inputs through user interactions with the user interface and present menu screens in response thereto, the user interactions including at least one of button and/or touchscreen presses;
a memory for storing operating parameters and data relating to operation of the delivery mechanism; and
a processor disposed in the housing and configured to process user inputs received at the user interface and to control the delivery mechanism based on the user inputs, the processor further configured to:
place the device in an operating mode;
control the delivery mechanism and present menu screens on the user interface in response to user inputs received through user interactions with the user interface while in the operating mode;
detect pump parameter and data values when the user inputs are received; and
write the user interactions including the button and/or touchscreen presses and pump parameter and data values into the memory; and
retrieve from memory the user interactions and the pump parameter and data values for play back on the user interface, including a menu screen by menu screen play back of the button and/or touchscreen presses on the user interface of the user previously navigating through menu screens on the user interface.

2. The ambulatory infusion pump of claim 1, wherein the processor is further configured to retrieve from memory the user inputs and the pump parameter and data values for transfer to a separate device.

3. The ambulatory infusion pump of claim 1, wherein the processor is further configured to write the user inputs received and pump parameter and data values into the memory for a predetermined period of time following a first user input.

4. The ambulatory infusion pump of claim 1, wherein the user inputs comprise a plurality of discrete user inputs separated from each other in time.

5. The ambulatory infusion pump of claim 1, wherein the pump parameter and data values include a glucose level of the user.

6. The ambulatory infusion pump of claim 1, wherein the pump parameter and data values include a time and date.

7. The ambulatory infusion pump of claim 1, wherein the processor is further configured to analyze the user inputs received and pump parameter and data values in the memory and provide at least one recommendation to the user based on the analysis.

8. The ambulatory infusion pump of claim 2, wherein the processor is further configured to receive at least one recommendation from the separate device based on the user inputs and the pump parameter and data values and to display the at least one recommendation to the user on the user interface.

9. An ambulatory infusion pump comprising:
at least one control feature that receives a user input through user interactions at a time during operation in an operating mode in which the pump performs actions in response to the user input, the user interactions including at least one of button and/or touchscreen presses; and
a processor that detects the received user input from the control feature at the time of the received user input and presents menu screens on a user interface in response thereto while the pump operates in the operating mode, detects pump parameter values at the time of the received user input, and writes the received user input including the button and/or touchscreen presses and the pump parameter values into memory of the pump, wherein the processor is configured to retrieve from memory the user input including the user interactions and the pump parameter values for play back on the user interface, including a menu screen by menu screen play back of the button and/or touchscreen presses on the user interface of the user previously navigating through the menu screens.

10. The ambulatory infusion pump of claim 9, wherein the processor is configured to retrieve from memory the user input and the pump parameter values for transfer to a separate device.

11. The ambulatory infusion pump of claim 9, wherein the processor is configured to write the received user input received and pump parameter values into the memory or a predetermined period of time following a first user input.

12. The ambulatory infusion pump of claim 9, wherein the user input comprises a plurality of discrete user inputs separated from each other in time.

13. The ambulatory infusion pump of claim 9, wherein the pump parameter values include a glucose level of the user.

14. The ambulatory infusion pump of claim 9, wherein the pump parameter values include a time and date.

15. The ambulatory infusion pump of claim 9, wherein the processor is configured to analyze the received user input and pump parameter values in the memory and provide at least one recommendation to the user based on the analysis.

16. The ambulatory infusion pump of claim 10, wherein the processor is further configured to receive at least one recommendation from the separate device based on the user input and the pump parameter values and to display the at least one recommendation to the user on a user interface of the pump.

17. An ambulatory infusion pump, comprising:
a housing;
a delivery mechanism at least partially contained within the housing and adapted to facilitate delivery of fluid to a user;
a user interface adapted to receive user inputs through user interactions with the user interface and present menu screens in response thereto;
a memory for storing operating parameters and data relating to operation of the delivery mechanism; and
a processor disposed in the housing and configured to process user inputs received at the user interface and to control the delivery mechanism based on the user inputs, the processor further configured to:
place the device in an operating mode;
control the delivery mechanism and present menu screens on the user interface in response to user inputs received through user interactions with the user interface while in the operating mode;
detect pump parameter and data values when the user inputs are received; and
write the user interactions and pump parameter and data values into the memory, including a menu screen by menu screen sequence of the user interactions of the user previously navigating through menu screens on the user interface.

18. The ambulatory infusion pump of claim 17, wherein the processor is further configured to retrieve from memory the menu screen by menu screen sequence of user interactions and the pump parameter and data values for play back on the user interface.

* * * * *